United States Patent

Tanino et al.

[11] Patent Number: 4,656,455
[45] Date of Patent: Apr. 7, 1987

[54] HUMIDITY-SENSING ELEMENT

[75] Inventors: Katsumi Tanino, Takaoka; Norihiro Kiuchi, Hachioji; Chikara Tominaga, Yokohama; Eiji Itoh, Urawa; Kiyoshi Ogino, Yono; Masataka Yahagi, Urawa; Masaru Sakamoto, Yono, all of Japan

[73] Assignees: Toyama Prefecture, Toyama; Nippon Mining Co., Ltd., Tokyo, both of Japan

[21] Appl. No.: 755,641

[22] Filed: Jul. 16, 1985

[30] Foreign Application Priority Data

Jul. 20, 1984 [JP] Japan ................... 59-149349
Oct. 2, 1984 [JP] Japan ................... 59-205539
Mar. 8, 1985 [JP] Japan ................... 60-44731
Mar. 14, 1985 [JP] Japan ................... 60-49452
Jun. 17, 1985 [JP] Japan ................... 60-130018

[51] Int. Cl.⁴ ............................... H01L 7/00
[52] U.S. Cl. ................... 338/35; 73/27 R; 73/29; 427/123; 427/125; 427/126.3
[58] Field of Search ............. 427/123, 125, 126.3; 73/27 R, 29; 338/34, 35

[56] References Cited

U.S. PATENT DOCUMENTS 4,307,373 12/1981 Johnston ............... 338/34
4,345,985 8/1982 Tohda ................... 427/125
4,582,657 4/1986 Shibata ................. 427/126.2

Primary Examiner—Richard Bueker
Attorney, Agent, or Firm—Seidel, Gonda, Goldhammer & Abbott

[57] ABSTRACT

A process for fabricating a humidity-sensing element comprises forming an electrode layer on at least one side of a ceramic substrate, applying to the electrode layer a humidity-sensitive paste containing a zirconia, zirconia-yttria, or yttria ceramic as a humidity-sensitive material, drying the coat, and then firing it at a temperature of 750° to 870° C. to form a humidity-sensing part.

11 Claims, 13 Drawing Figures

HUMIDITY-SENSING ELEMENT

BACKGROUND OF THE INVENTION

This invention relates to a process for fabricating a humidity-sensing element, and more specifically to a process for fabricating a humidity-sensing element of the electrical resistance type using ceramics based on $ZrO_2$, $ZrO_2+Y_2O_3$ and $Y_2O_3$. The humidity-sensing element according to this invention meets all the characteristic requirements for an element of this type, including low electrical resistivity, electrical resistance-humidity linearity, high sensitivity, and small variation with time. Moreover, it shows stable characteristics with very slight deviation of the electrical resistance-humidity characteristic curve in high and low humidity atmospheres, as well as in the ordinary humidity range.

Humidity-sensing elements in recent years have found widespread applications. With home appliances, they are often used in controlling the cooking by microwave ovens, determining the drying degrees of laundry in driers, monitoring humidity under control by air conditioners, and in detecting dewing of the cylinders in video taperecorders. For industrial applications, the elements are in widespread use for humidity control in the manufacture of various electronic parts. Among other fields in which they are finding use are air conditioning in agricultural greenhouses and prevention of dewing on rear-window defoggers of automobiles. For automated systems of food preparation, air conditioning, drying, and other operations, control of humidity, as well as of temperature, is now indispensable. Thus, there is a need for the development of humidity-sensing elements capable of functioning with higher reliability than heretofore.

In order to meet this requirement, humidity-sensing elements that utilize changes in electric resistance have come into use. They detect changes in the humidity content of a given object as changes in its electric resistance. The humidity-sensitive material so far proposed for sensor applications vary widely, from electrolytic substances typified by lithium chloride to organic polymers and ceramics. The humidity-sensing element of the resistance type is basically required to offer a low electrical resistance, good linearity of the resistance-humidity characteristic, proper operating range, and resistance to deterioration in the service environments. Ceramics have recently attracted growing attention as materials for humidity-sensing use, generally satisfying all the foregoing requirements.

As to the fabrication of the humidity-sensing elements, two types have been proposed. One is a bulk type in which a pair of electrodes is disposed on opposite sides of a ceramic sintered body. The other is a thick film type fabricated by forming an electrode layer on at least one side of a ceramic substrate, applying a mixture of the powder of the above ceramic substance with a binder to the electrode layer, and drying and sintering the coat to form a solid humidity-sensing part.

The literature on ceramic humidity-sensing elements includes the following:
Japanese Patent Application
Public Disclosure Nos. 152105/1982, 47703/1984, 166701/1983, 86447/1983.

SUMMARY OF THE INVENTION

While a variety of ceramic materials have so far been proposed as humidity-sensitive materials, they are required to have important characteristics in common as follows:

(A) Appropriately low electrical resistance (The greater the current the better the sensitivity.)
(B) Good resistance-humidity characteristic linearity
(C) High sensitivity
(D) High precision
(E) High stability
(F) Adequate reproducibility In view of these and other requirements, varied ceramic materials have been studied for use in humidity-sensing units.

As the ceramic humidity sensor materials that basically satisfy these characteristic requirements, we have arrived at a conclusion that following ceramics based on yttria ($Y_2O_3$), $Y_2O_3$ plus zirconia ($ZrO_2$), and $ZrO_2$ give good results.

(1) $Y_2O_3$,
(2) $Y_2O_3+ZrO_2$ (0.01–99.00%),
(3) $Y_2O_3$+at least one of (CaO, MgO, BaO, $TiO_2$, $Ta_2O_3$, $Nb_2O_3$, and $V_2O_5$) (0.01–99.00%), and
(4) $ZrO_2$+at least one of (CaO, MgO, BaO, $TiO_2$, $Ta_2O_3$, $Nb_2O_3$, and $V_2O_5$) (0.01–99.00%).

Of these ceramics, finally divided $Y_2O_3$ alone and stabilized $ZrO_2$ solid solution powders are particularly desirable in characteristics. powders" as used herein means finely divided solid solutions prepares beforehand by coprecipitation or other techniques in view of the fact that $ZrO_2$ forms a stable solid solution with at least one of $Y_2O_3$, calcia (CaO), and magnesia (MgO). Such a stabilized solid solution powder gives upon firing a humidity-sensing part of more homogeneous structure, and hence a humidity-sensing element of better stability than that made from an ordinary mechanically mixed powder.

It has also been found that remarkable improvements are achieved in the low resistivity, variation-with-time stability, and humidity response of the $ZrO_2$, $Y_2O_3+ZrO_2$, and $Y_2O_3$ type ceramic humidity-sensing elements by incorporating at least one of lithium carbonate ($Li_2CO_3$) and vanadium pentoxide ($V_2O_5$) into their humidity-sensing parts. These additives permit low-temperature firing of the ceramic material and produce a highly stable humidity-sensing part.

Further, surface treatment of the fired humidity-sensing part with potassium hydroxide (KOH) or sodium carbonate ($Na_2CO_3$) is helpful in increasing the stability. Treatment with KOH is preferred. Surface treatment with KOH as an after-treatment tends to cause a scatter in the degrees of KOH impregnation, or involves difficulties in thoroughly impregnating the humidity-sensing part with the KOH. For these reasons it is more effective to perform it not as an aftertreatment but as a pretreatment in which the starting material powder is impregnated beforehand with a KOH solution. In this case, pretreatment with potassium oxide ($K_2O$) or potassium carbonate ($K_2CO_3$) may replace the treatment with KOH.

The humidity-sensing elements of this character are exposed to atmospheres in diversified service environments to detect the water vapor contained therein. Liquid water, soot, exhaust emissions, cement dust, pollen, and other miscellaneous particulates from the atmospheres can deposit on the humidity-sensing parts of the elements to deterioate their performance. Above all, deposition of water is most objectionable for the humidity-sensing elements.

One approach for the protection of humidity-sensing elements against water and dust is the use of a filter. A wide variety of filters have been proposed including filter films of specific resins which wrap up the elements, tubular sintered bodies of AS or ABS resin powder covering the elements, thick $MnWO_4$ films coating the humidity-sensing parts, hydrated, hardened cement layers, and foamed metal covers.

A common disadvantage associated with the use of filters as protector means is poor response of the filtered humidity-sensing elements. The filters must effectively keep off water, dust, and other objectionable matter while, at the same time, rapidly the atmosphere, the humidity of which is to be measured, admitting into contact with the humidity-sensing part.

We judged that, in principle, a very thin porous film filter of a polymeric material is optimum for the above purposes, and we have studied the material and pore characteristics. Previously, films of fluorine resin, polyethylene, polypropylene, and silicone resin were specifically selected as satisfactory polymeric filter films, tetrafluoroethylene and polypropylene resin films being most preferred (Japanese Pat. App. Pub. Discl. No. 86447/1983). Our further investigations have revealed that a chlorinated polymer film that satisfies the following conditions gives even better response.

(1) Porosity: 34–85%
(2) Pore size: 0.01–3 $\mu m$
(3) Thickness: 20–200 $\mu m$ This filter film is attached to a window formed at least opposite to the humidity-sensing part of a case in which the humidity-sensing element is housed.

DETAILED DESCRIPTION

Figure 1:
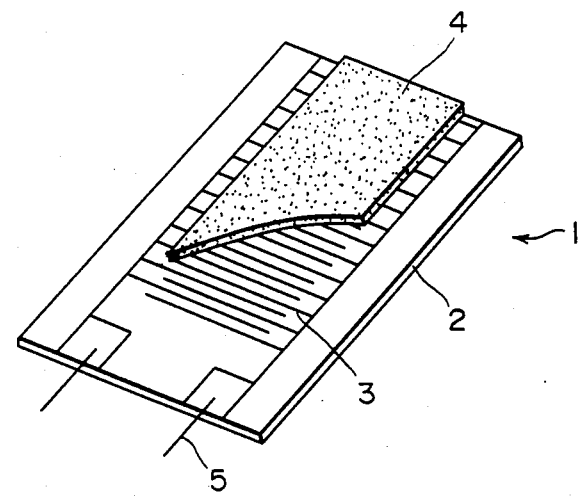
FIG. 1 is a perspective view of a thick-film humidity-sensing element, with the humidity-sensing part partly cut away.

While the humidity-sensing element according to this invention may be embodied as an assembly of the type consisting of a ceramic sintered body formed with a pair of electrodes on its opposite sides, it is preferably fabricated as a thick film type having a humidity-sensitive film on a substrate. FIG. 1 illustrates such a humidity-sensing element of the thick film type. The element 1 comprises a substrate 2, an electrode part 3 formed on one side or both sides of the substrate, and a humidity-sensing part 4 further formed thereon (the humidity-sensing part being partly broken away). Lead wires are designated at 5. The substrate to be used is a ceramic, such as of $Al_2O_3$, $SiO_2$, or $ZrO_2$. The electrode layer on the substrate is formed of gold, silver, platinum, or ruthenium by screen printing, vacuum deposition, or photoetching.

The varied microprocessing techniques in use for the fabrication of printed circuit boards for electronic circuitry may be employed to advantage in forming fine electrode patterns. For example, sputtering is a useful means. A desirable pattern is, as shown in FIG. 1, in the form of a pair of comblike electrodes overlapped opposite to each other, with their teeth engaged alternately and in parallel. The shorter the spacing between the teeth, the lower the resistance, and hence the higher the sensitivity, of the humidity-sensing element. Experiments showed that tooth-to-tooth spacings in the range of 0.05 to 0.20 mm give good results.

Notably, comb electrodes of gold are helpful in lowering the resistance of the resulting humidity-sensing element. The gold electrodes desirably are made by screen printing, although vacuum deposition is preferred where microminiaturization of the element is a necessity.

Under the invention the material to constitute the humidity-sensing part is a ceramic chosen from $ZsO_2$, $ZrO_2+Y_2O_3$, and $Y_2O_3$ types, which includes:

(1) $Y_2O_3$,
(2) $Y_2O_3+ZrO_2$ (0.01–99.00%),
(3) $Y_2O_3+$at least one of ($CaO$, $MgO$, $BaO$, $TiO_2$, $Ta_2O_3$, $Nb_2O_3$, and $V_2O_5$) (0.01–99.00%), and
(4) $ZrO_2+$at least one of ($CaO$, $MgO$, $BaO$, $TiO_2$, $Ta_2O_3$, $Nb_2O_3$, and $V_2O_5$) (0.01–99.00%).

Particularly desirable are $Y_2O_3$ and $ZrO_2+Y_2O_3$. An even more desirable humidity-sensitive material is stabilized $ZrO_2$.

By stabilized $ZrO_2$ is meant the composition of a solid solution of $ZrO_2$ with at least one of $Y_2O_3$, $CaO$, and $MgO$, which, in the phase diagram, is within the $ZrO_2$ side solid-solution region. A $ZrO_2+Y_2O_3$ system is desirable. The proportion of $Y_2O_3$ to be added may range from 10 to 60% by weight. The powdered $ZrO_2+Y_2O_3$ solid solution is prepared, for example, by effecting a coprecipitation reaction of a mixture of given proportion of $ZrOCl_2$ and $YCl_3$ with an alkali such as ammonia ($NH_3$), thus forming a solid solution of $Y_2O_3$ in $ZrO_2$ at the stage of material powder to obtain a uniformly mixed powder. Aside from the coprecipitation, other methods such as hydrolysis, alkoxide processes, and melting methods may be used in producing the solid solution powder. It is preliminarily fired at 600° to 800° C., and fired at a higher temperature of 900° to 1100° C., and then ground to less than 625 mesh in size by a ball mill or the like to obtain the powdered starting material.

The $ZrO_2$, $ZrO_2+Y_2O_3$, or $Y_2O_3$ ceramic powder thus obtained is mixed, where necessary, with a binder, and the powder or mixture is ground and kneaded into a humidity-sensitive paste, after viscosity adjustment with a resinous painting material. The paste is then applied to the electrode layer. The humidity-sensing part may contain at least either of $Li_2CO_3$ and $V_2O_5$. Surface treatment of the humidity-sensing part with KOH or $Na_2CO_3$ is beneficial.

A preferred example of fabrication of a humidity-sensing element using a stabilized $ZrO_2$ powder, for instance, will now be explained. Desirably, the starting material powder is pretreated by addition and reaction of at least one of KOH, $K_2O$, and $K_2CO_3$, the treatment with KOH being preferred. The KOH treatment involves immersion of the powder with stirring in a solution at a KOH concentration of 5 to 20% by weight for 1 to 20 minutes. In this way a powder containing 1 to 10% by weight of KOH is obtained.

The powder pretreated by impregnation with KOH is then filtered, dried, and subjected to primary firing at a temperature of 800° to 1150° C.

To improve the stability, accuracy, and sensitivity of the resulting humidity-sensing element, it is desirable to add at this stage 1 to 5 mol% of $Li_2CO_3$ to the powder. For these effects the addition of at least 1 mol% of the compound is necessary. However, the addition of more than 5 mol% is detrimental in that it increases the resistance of the element to excess. $V_2O_5$ may be employed instead.

After the mixing, secondary firing of the mixture is done at 700° to 900° C., and the resultant is ground again.

The powder so obtained is thoroughly kneaded with the addition of a suitable resinous painting material, and the viscosity is adjusted with ethyl acetate or the like to yield a paste for humidity-sensing use.

The humidity-sensitive paste thus prepared is applied by screen printing to the electrode layer to form a coating film thereon which will have a final film thickness of 5 to 200 μm, preferably 20 to 50 μm.

After drying, the coating film is fired at a temperature between 500° and 870° C., typically at 700° to 870° C. The firing is carried out for 5 to 90 minutes, usually a period of 8 to 30 minutes being adequate. This treatment sinters the ceramic particles to give a backbone and impart structural strength to the humidity-sensitive film. Heretofore, a firing temperature at 900° C. at the lowest has been believed necessary to confer the desired structural strength on the product, but it is now known that such high-temperature firing rather impairs the performance, notably the electrical resistance, of the humidity-sensing element. According to the invention, therefore, the firing is conducted at a temperature below 870° C. High-temperature firing as in the part fuses (slags) the ceramic particles or binder to decrease the porosity, affect the response, and increase the electrical resistance of the resulting element. In addition, it tends to transform the ceramic material of the invention into an instable crystalline form, thus possibly causing lack of stability in the ceramic. These possibilities are precluded by fixing the upper limit of 870° C. to the firing temperature range. Even such low-temperature firing assures the desired structural strength of the humidity-sensing element.

The humidity-sensitive film having been formed in this way, a sequence of assembling steps, that is, soldering, aging, casing, and marking, is followed to complete the element. For the aging, a temperature of 50° to 90° C., preferably 60° to 85° C., is used. The aging treatment renders the element stable with little deterioration under its service conditions.

Instead of the pretreatment with KOH, an aftertreatment of the humidity-sensing part just formed may be performed by immersing the part into a solution of KOH or $Na_2CO_3$, preferably KOH, and then firing the impregnated part. The pretreatment is preferred, however, because the KOH impregnation aftertreatment tends to cause nonuniform impregnation, and it is difficult to allow the KOH to permeate through the entirety of the humidity-sensing part. Furthermore, it is to be noted that a single element substrate is printed, for instance, with 24 elements. If it is KOH-treated after the humidity-sensitive film has been formed thereon, not only the printed substrate, but also the conductor pad to which lead pins are to be later attached, is treated alike. This is undesirable because of its adverse effect on subsequent soldering. The unfavorable effect upon solderability is avoided by the KOH treatment of the humidity-sensitive powder prior to its firing.

Such a humidity-sensing element is exposed to the atmosphere of the service environment that can vary widely. The element detects the water vapor contained in the particular atmosphere. Its performance deteriorates as liquid water, soot, exhaust matter, cement dust, pollen, and other particulates from the atmosphere deposit on the humidity-sensing part of the element. Above all, deposition of water can be fatal to the element.

In order to prevent the deposition of water, dust, and other foreign matter on the humidity-sensing part, the element is desirably encased in a container having a window fitted with a filter film and formed in the portion of a case facing the humidity-sensing part of the element.

Figure 2:
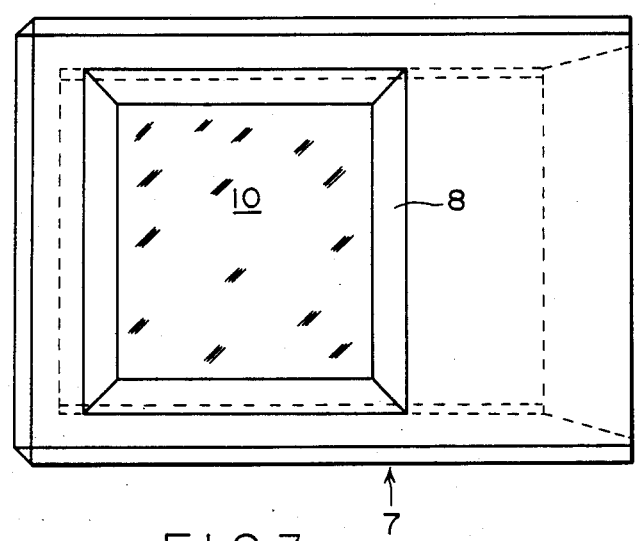
FIG. 2 is a plan view of a case accommodating the humidity-sensing element.
Figure 3:
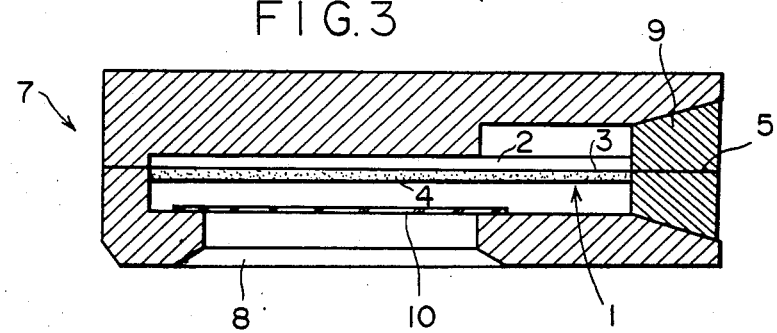
FIG. 3 is a cross sectional view along the longitudinal centerline of the unit shown in FIG. 2.

FIGS. 2 and 3 illustrates such a case with a filter window containing the humidity-sensing element 1 of FIG. 1.

The case 1 containing the humidity-sensing element comprises two housing halves, upper and lower, which sandwich the element in between. The case is made of a plastic material such as a polypropylene or ABS resin. It is formed with a window 8 facing at least the humidity-sensing part 4 of the element. To this window 8 is fitted a filter film 10 in accordance with the invention. Desirably, the filter film 10 is secured to the peripheral edges of the window by hotmelt or ultrasonic bonding, pressure welding, or other technique. The numeral 9 indicates a base supporting the humidity-sensing element through which lead wires 5 extend. The housing halves of the case are joined by fusing along the mating edges.

The filter film 10 according to the invention is a thin film of a chlorinated polymer, typically of chlorinated ethylene. The thin chlorinated polymer film is formed by dissolving a chlorinated polymer in a solvent, spreading the solution into a sheet, and then evaporating off the solvent from the sheet. When necessary, it may contain an oil and/or a surface active agent. Such a film is commercially available.

The film must be as thin as 20 to 200 μm in thickness. A film thickness in this range is appropriate for forming bent or curled pores inside the film, yet securing good response. The porosity should range from 35 to 85%. A porosity of less than 35% would affect the response unfavorably, whereas a porosity in excess of 85% would reduce the film strength and lessen the di-dusting and waterproofing effects. The pore size is selected from the range of 0.01 to 3 μm which will allow the passage of water vapor but not cement particles, liquid water, spray droplets, and foreign particles ranging in diameter from 1.00 to 10 μm.

The water repellency and other properties of the chlorinated polymer combine with the pore characteristics specified above to enable the filter film effectively to keep off liquid water and dust in the working atmosphere from the humidity-sensing part. Nevertheless, the element response remains unimpaired because the filter film permits rapid passage of water vapor in the atmosphere. The advantages associated with the use of the chlorinated polymer film as the filter may be summarized as follows:
1. Deterioration of performance with deposits of water and dust can be prevented for long periods of time, practically without marring the response.
2. Since the filter film is bonded to the case by hot-melt bonding or other technique, the unit is simple in construction and is easy to assemble.
3. This humidity sensor is employable in almost all service environments because the chlorinated polymer film has a critical service temperature (the temperature at which the pores begin to break) of as high as 180° to 190° C.

EXAMPLE 1

An 85wt%$ZrO_2$—15wt%$Y_2O_3$ solid solution powder was produced by coprecipitation and preliminarily fixed at 800° C. Then, the steps below were followed, in the descending order, to prepare a paste for humidity-sensing use.

Starting with the firing:

| | |
|---|---|
| Grinding (wet) | by a ball mill, with the addition of ethyl alcohol. |
| ↓ | |
| Classification | −625 mesh, ethyl alcohol added. |
| ↓ | |
| Drying | at 60° C. for 5 hrs. |
| ↓ | |
| KOH impregnation | immersed in aqueous 15% KOH solution for 10 min. |
| ↓ | |
| Suction filtration | |
| ↓ | |
| Drying | |
| ↓ | |
| Primary firing | at 900° C. for 1 hr. |
| ↓ | |
| Addition of 1.5 mol % $Li_2CO_3$ | |
| ↓ | |
| Mixing & drying | Ethyl acetate added, and mixed for more than 1 hr. |
| ↓ | |
| Secondary firing | at 800° C. for 1 hr. |
| ↓ | |
| Grinding | |
| ↓ | |
| Kneading | with the addition of a resin, organic solvent, butyl carbitol, and ethyl acetate. |

Meanwhile, comblike gold electrodes were formed by screen printing on an $Al_2O_3$ substrate 18 mm long and 9 mm wide. The spacing between the comb teeth was 0.2 mm, and rows of electrode teeth were printed over a length of 12 mm.

The humidity-sensitive paste prepared above was applied to this electrode layer by screen printing. The coat was dried in two stages, at 160° C. for 50 minutes and then at 330° for 50 minutes, and then was fired at 800° C. for 12 minutes. The final film thickness attained was 30 μm.

After soldering, the fabricated unit was aged in a thermostat at 80° C. and at a relative humidity of 60%.

Figure 5:
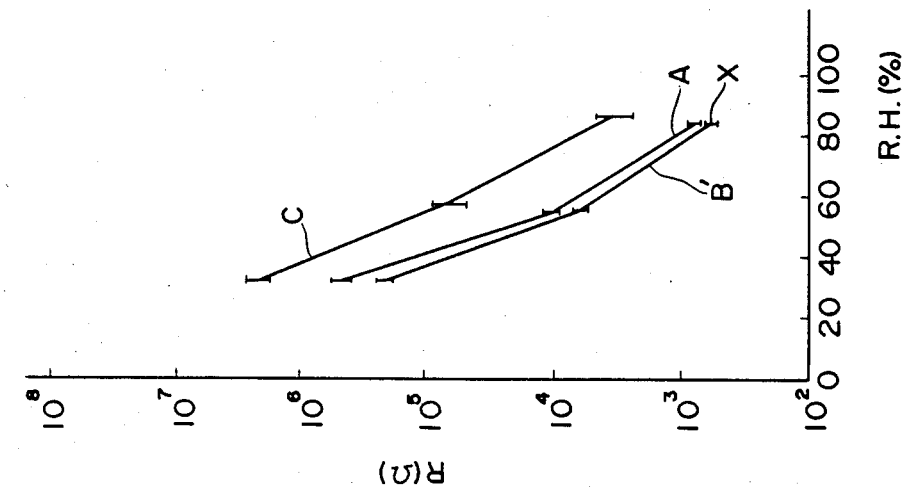
FIGS. 4 and 5 are graphs showing the resistance-humidity characteristics of humidity-sensing elements using stabilized $ZrO_2$ powder and pretreated with KOH.
Figure 4:
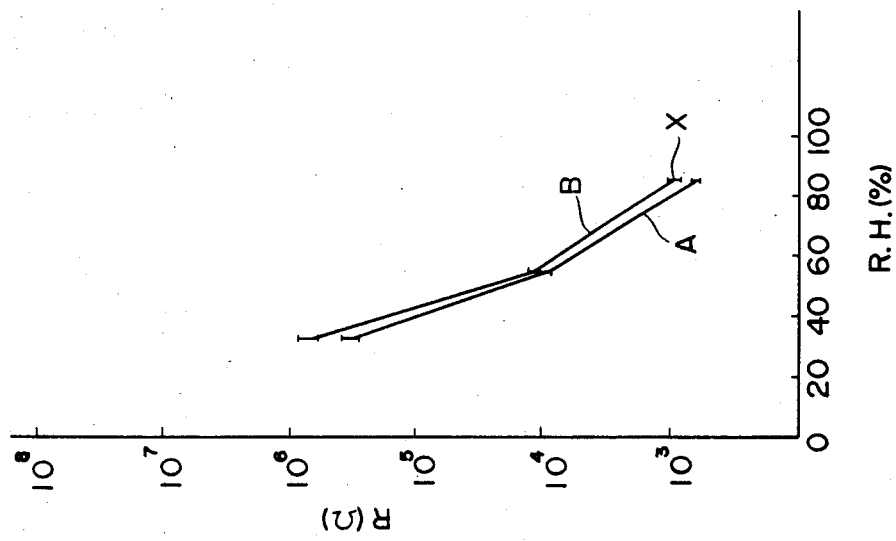

FIG. 4 shows the results of high-temperature, low-humidity standing tests of the element thus obtained, and FIG. 5 shows the results of high-temperature, high-humidity standing tests. The measuring temperature used was 25° C. In these graphs, each curve A represents the characteristics of the aged specimen, and curve B represents the characteristics of the specimen aged and then allowed to stand at 80° C. and 30%RH for 48 hours. The curve B' represents the characteristics of the specimen aged and allowed to stand at 80° C. and 90%RH for 12 hours. The graphs indicate good stability and accuracy (±3.5%).

FIG. 5 includes the characteristics of a specimen in which the gold electrodes were replaced by $RuO_2$ electrodes, represented by the curve C. It indicates that the specimens using gold electrodes exhibit lower resistances.

The test specimens shown in FIGS. 4 and 5 used humidity-sensing powder pretreated with KOH, and therefore the scatter is satisfactorily narrow as indicated at X in these graphs. The scatter was n=5 according to experiments.

EXAMPLE 1-1

Figure 6:
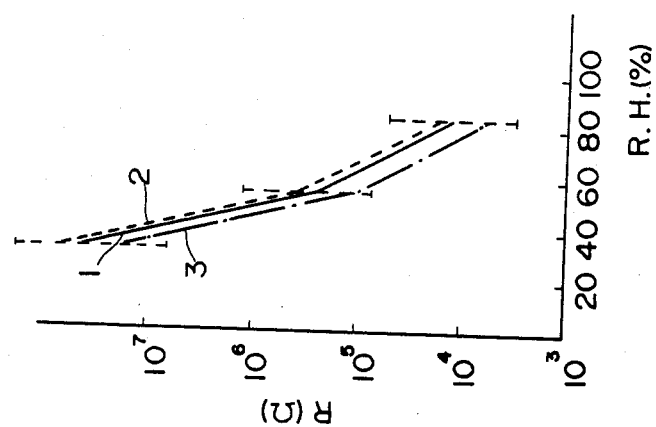
FIG. 6 is a graph similar to FIGS. 4 and 5 but of elements aftertreated with KOH.

In order to see the advantages of the pretreatment with KOH over the aftertreatment with the same, the procedure described in Example 1 was followed using the same solid solution powder with the exception that the KOH treatment was done after the firing of the humidity-sensitive film and $RuO_2$ electrodes were employed instead. The resistance-humidity-sensing characteristics of the test specimens thus obtained are graphically shown in FIG. 6 (the measurement temperature being 25° C.). The curve 1 represents the characteristics immediately after aging, the curve 2 the characteristics after aging and standing at 80° C. and 30%RH for 48 hours (low-humidity test), and the curve 3 the characteristics after standing at 80° C. and 90%RH for 12 hours (high-humidity test). The use of $RuO_2$ electrodes resulted in lower resistance and accuracy values (±5%) than those of the specimens pretreated with KOH. In addition, wider scatter of the product qualities resulted.

EXAMPLE 1-2

Figure 7:
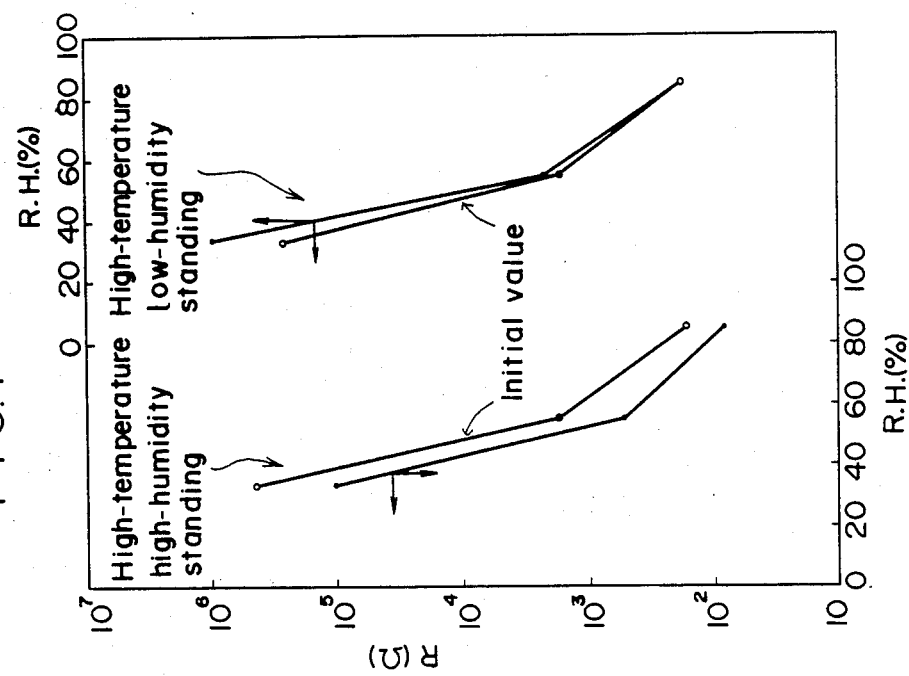
FIGS. 7 and 8 are graphs similar to FIGS. 4 and 5 but of elements treated with different KOH concentrations of 20 and 30 wt%, respectively.
Figure 8:
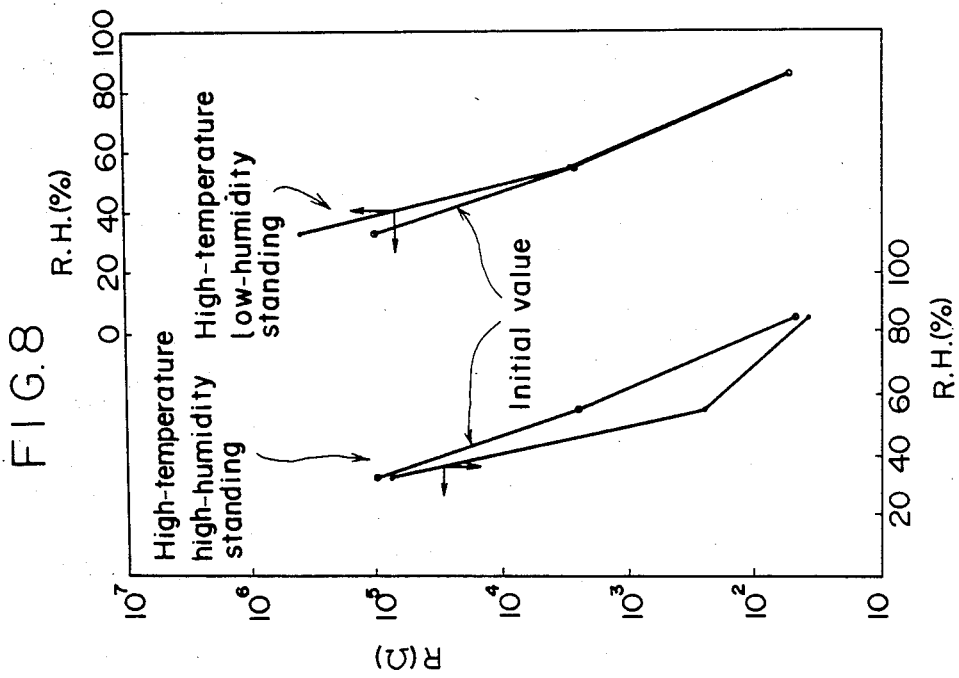

Test specimens of humidity-sensing elements were fabricated by repeating the procedure of Example 1 except that the concentration of KOH in the aqueous solution was increased to 20% and 30% by weight. The specimens were likewise subjected to high-temperature/low-humidity and high-temperature/high-humidity standing tests. The test conditions were identical. The results are given in FIG. 7 (using the 20 wt% KOH solution) and FIG. 8 (using the 30 wt%KOH solution). The graphs clearly show that too high a KOH concentration produces very poor high-temperature test results.

EXAMPLE 2

Comblike ruthenium electrodes were screen printed on an $Al_2O_3$ substrate 18 mm long and 9 mm wide. The comb-tooth spacing of the electrodes was 0.13 mm and the print extended over a length of 12 mm. A humidity-sensing layer of a mixture consisting of 93% $Y_2O_3$ and 7% leadless borosilicate glass was formed over the electrode layer, in the following manner. The mixture was ground was kneaded on an automatic mortar of alumina, and its viscosity was adjusted with butyl carbitol and an epoxy resin coating material, and then was applied to the electrode layer by screen printing so that a humidity-sensing layer about 20 μm thick could result. Thereafter, the coat was predried at 170° C. for one hour and sintered at 850°±10° C. for 30 minutes.

Figure 9:
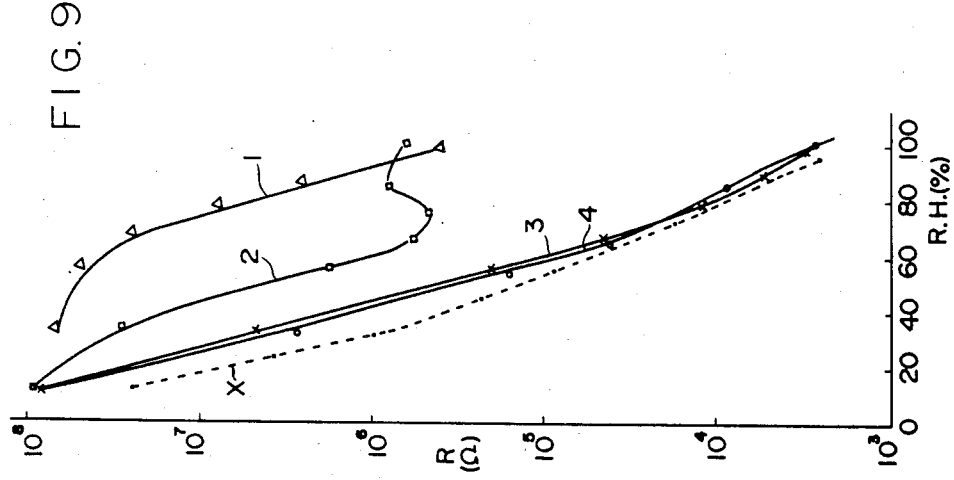

The changes in resistance with humidity of the humidity-sensing element thus fabricated were measured using a measuring frequency of 1000 Hz and a measuring voltage of 1V. The characteristic curve obtained is designated X in FIG. 9. For comparison, FIG. 9 shows also the characteristics of some commercially available products. The materials and structures of the conventional elements tested were as listed below:

| Comparative specimen No. | Material | Structure |
|---|---|---|
| 1 | $MgCr_2O_4 - TiO_2$ | Bulk type |
| 2 | $Al_2O_3 + TiO_2$ | Thin-film-comblike |
| 3 | $TiO_2 + V_2O_5$ | Thin-film-comblike |
| 4 | Resin type | Thin-film-comblike |

The resistance-humidity characteristics of the product according to the invention are such that the resistance is lower than those of the commercially available products 1 to 4. Linearity is better, too.

Figure 10:
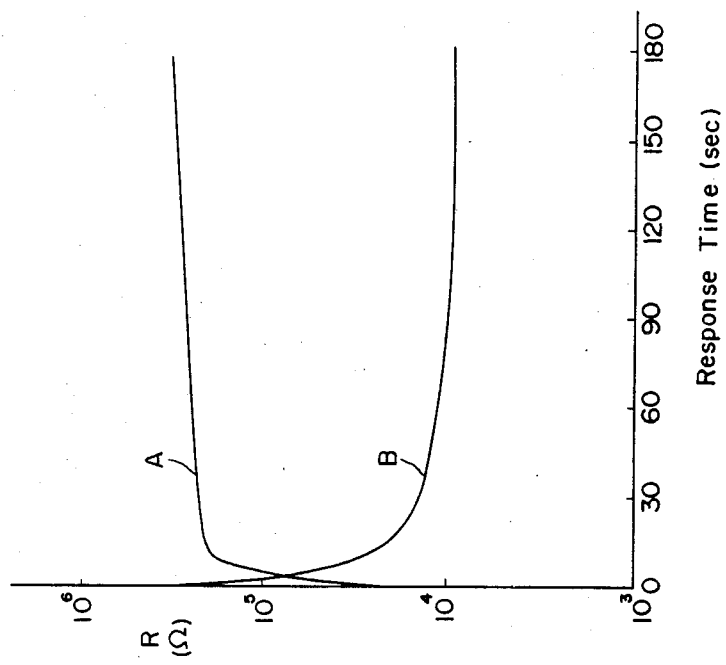
FIGS. 9 and 10 are graphs showing the resistance-humidity characteristics and response, respectively, of humidity-sensing elements using $Y_2O_3$ alone.

Next, the humidity-sensing response characteristics of the element of the invention are given in FIG. 10. The curve A represents the response with a change in relative humidity from 85% down to 30%, and the curve B represents the response with a change from 30% up to 85%. The shorter the time required to reach an equilibrium, the better the response. Both the curves A and B show adequately short response time.

As explained above, employing the humidity-sensitive material of $Y_2O_3$ alone eliminates the need of such a post-sintering treatment as immersion coating, and renders it possible to obtain a ceramic humidity-sensing element of the electric resistance type which combines low resistance with desirable linearity and response.

EXAMPLE 3

On an $Al_2O_3$ substrate having a length of 18 mm and a width of 9 mm, comblike ruthenium electrodes were formed by screen printing. The electrodes, with a comb-tooth spacing of 0.20 mm, were printed over a length of 12 mm. Further, over this electrode layer was formed a humidity-sensing layer of a mixture consisting of 93% ceramic mixture and 7% leadless borosilicate glass, the ceramic mixture in turn consisting of $Y_2O_3$ and $ZrO_2$ at a weight ratio of 50:50. The humidity-sensing layer was formed in the following way. The ceramic-glass mixture was ground and kneaded on an automatic mortar of alumina, its viscosity was adjusted with butyl carbitol and an epoxy resin coating material, and the resulting mixture was screen printed on the electrode layer to form an about 20 μm-thick humidity-sensing layer. The coat was the predried at 170° C. for one hour and fired at varying temperatures in the range of 800° to 900° C. for 15 minutes.

Figure 11:
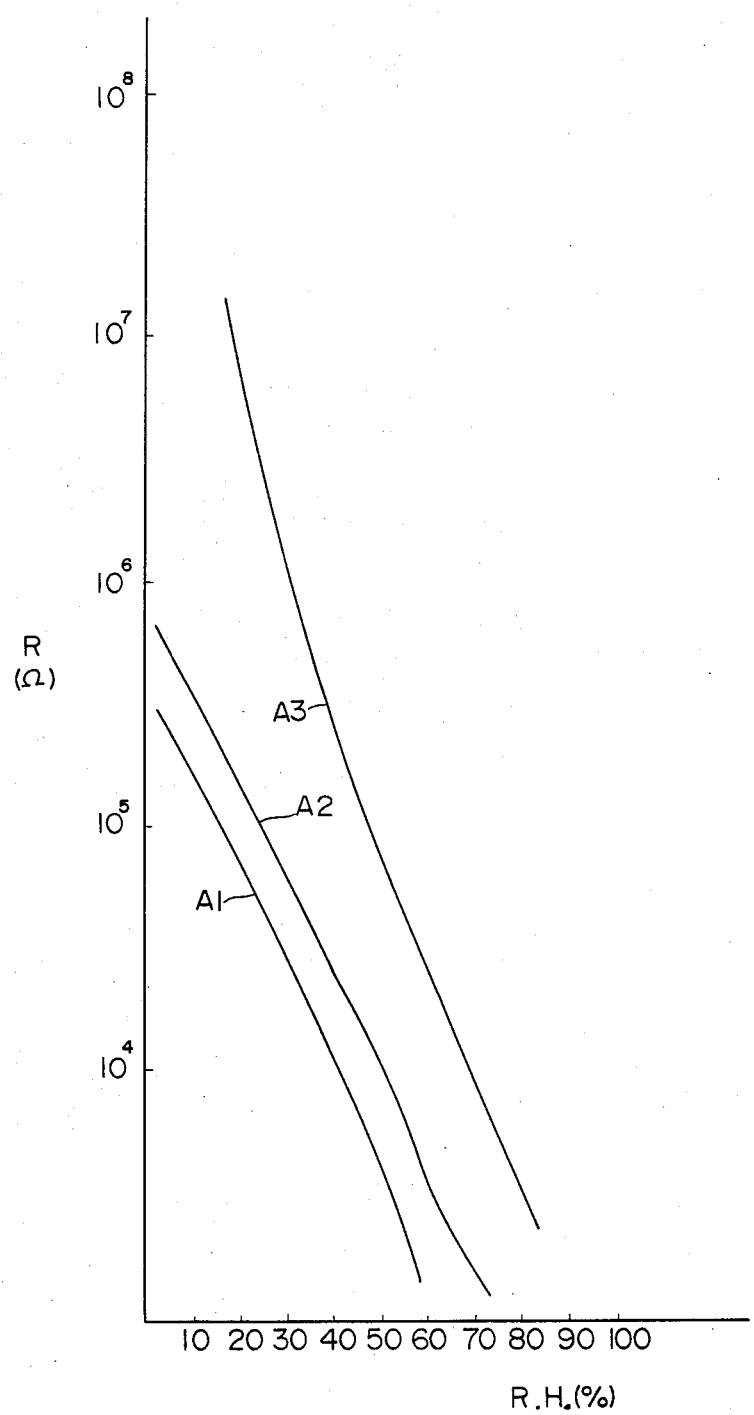
FIG. 11 is a graph showing the influence of firing temperature upon the resistance-humidity characteristics.

The changes in the resistance with the humidity of the test specimens were determined with a measuring frequency of 1000 Hz and measuring voltage of 1V. The characteristic curves thus obtained are shown in FIG. 11, as the curve $A_1$ (firing temp. 800° C.), curve $A_2$ (850° C.), and as the curve $A_3$ (900° C.) of a comparative example. It will be appreciated that lowering the firing temperature below 900° C. reduces the electrical resistance of the resulting element.

EXAMPLE 4

Comblike electrodes of ruthenium paste were formed by screen printing on an alumina substrate about 14 mm long and 9 mm wide. With a comb-tooth spacing of 0.2 mm, the rows of electrode teeth were printed over a length of 8 mm. A humidity-sensitive paste containing a $ZrO_2$—$Y_2O_3$ ceramic mixture and a binder was applied by screen printing over the electrodes. Drying of the coat was followed by firing at 800° C., treatment with KOH by immersion, firing at 800° C., and aging, in the order of mention, to fabricate a humidity-sensing element.

This humidity-sensing element was placed into a case of polypropylene as shown in FIGS. 2 and 3. The case was formed with a window having an inner dimension of 7.5 mm² facing the humidity-sensing part. A "Yumicron membrane filter MF-250"(trade designation of a chlorinated ethylene film manufactured by Yuasa Battery Co.) was attached by hotmelting to the window frame. This film had a thickness of 1.00 μm, porosity of 60%, and pore size of 0.1 to several microns.

Figure 12:
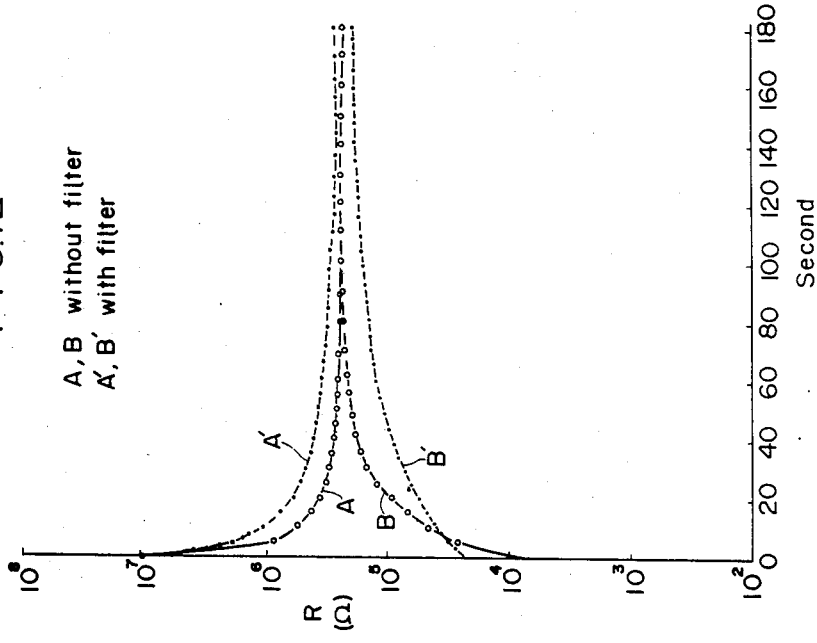

The humidity sensor thus fabricated was put in actual service for three weeks and then its humidity-sensing part was inspected. It carried substantially no deposit. Further, the response of this humidity sensor was determined under different conditions, by changing the humidity from 33% up to 55% (A), and changing it from 85% down to 55% (B), as graphically represented in FIG. 12. It is obvious that there are appreciable differences between the results with the test specimens without filter (A & B) and those of the specimens equipped with the filter (A' & B'). This means that the response of the sensor is not interrupted by the presence of the filter film.

EXAMPLE 4-1

Figure 13:
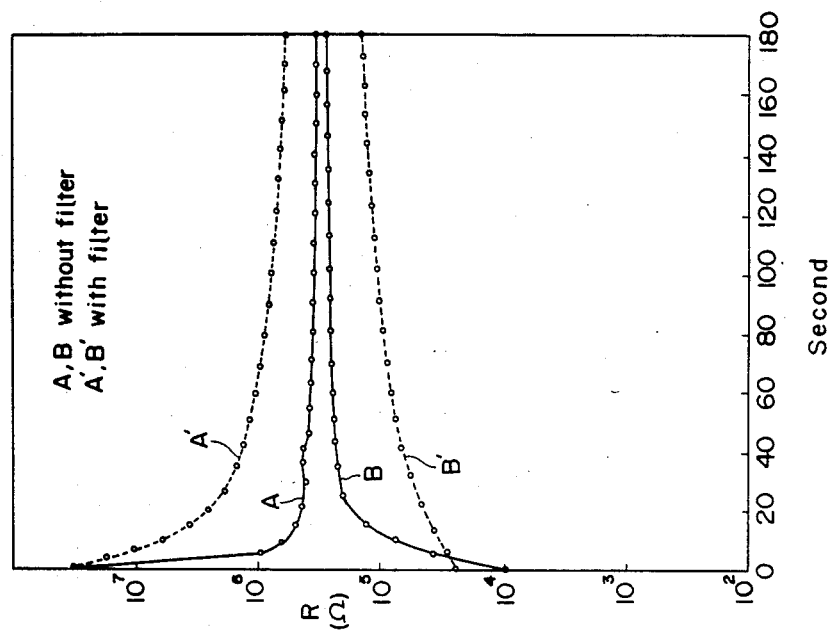
FIGS. 12 and 13 are graphs showing the responses of humidity-sensing elements using chlorinated ethylene film and polypropylene sintered filters, respectively.

Response characteristics were investigated under the same conditions as used in Example 1 except that a polypropylene sintered filtered (1.5 mm thick with a pore size of 200 to 250 μm and porosity of 80%) was employed. FIG. 13 summarizes the results. The graph clearly shows wide discrepancies between the response curves without filter (A & B) and with the filter (A' & B').

EXAMPLE 4-2

A commercially available dust-arresting mesh filter using special monofilaments was employed. The mesh size was too large for the resulting element to be of practical use.

What is claimed is:
1. A process for fabricating a humidity-sensing element which comprises the steps of
   forming a gold electrode layer in a pattern of twin combs on at least one side of a ceramic substrate,
   preparing a humidity-sensing paste by preliminarily firing a powder of a stabilized solid solution comprising $ZrO_2$ and $Y_2O_3$ at 600° to 800° C., fully firing the powder at 900° to 1100° C., grinding the fired powder into finer particles of =625 mesh, immersing the powder in a 5 to 20% weight percent KOH solution thereby allowing the powder to acquire 1 to 10% by weight of KOH, primarily firing the KOH-containing powder at 800° to 1150° C., adding 1 to 5 mol% of $Li_2CO_3$, secondarily firing the powder at 700° to 900° C., regrinding, and thoroughly kneading the powder with the addition of a suitable resin material to adjust the viscosity of the resulting paste, applying the humidity-sensitive paste thus prepared to the electrode layer by screen printing, to form a coat on the electrode layer, and drying and firing the coat at 500° to 870° C. to form the humidity-sensing part of the humidity-sensing element.

2. A process according to claim 1 wherein said humidity-sensing element is housed in a case equipped with a filter film of a chlorinated polymer.

3. A process for fabricating a humidity-sensing element which comprises forming an electrode layer on at least one side of a ceramic substrate, applying to the electrode layer a coat of a humidity-sensitive paste containing a ceramic comprising $ZrO_2$, $Y_2O_3$, or mixtures thereof with a member of the group consisting of $Li_2CO_3$ and $V_2O_5$ as a humidity-sensitive material, drying the coat, and then firing the coat at a temperature of 750° C. to 870° C. to form the humidity-sensing part of the humidity-sensing element.

4. A process according to claim 3, wherein said humidity-sensitive paste contains 1 to 5 mol% of $Li_2CO_3$.

5. A process for fabricating a humidity-sensing element which comprises forming an electrode layer on at least one side of a ceramic substrate, pretreating a humidity-sensitive material containing a ceramic comprising $ZrO_2$, $Y_2O_3$ or mixtures thereof by reacting said material with at least one of KOH, $K_2O$ and $K_2CO_3$, applying to the electrode layer a coat of a paste of said humidity-sensitive material, drying the coat, and then firing the coat at a temperature of 750° C. to 870° C. to form the humidity-sensing part of the humidity-sensing element.

6. A process according to claim 5 wherein said humidity-sensitive material is immersed in a solution of KOH at a concentration of 5 to 20% by weight and then fired so as to contain 1 to 10% by weight of KOH.

7. A process for fabricating a humidity-sensing element which comprises forming an electrode layer on at least one side of a ceramic substrate, applying to the electrode layer a coat of a humidity-sensitive paste containing a ceramic comprising $ZrO_2$, $Y_2O_3$, or mixtures thereof as a humidity-sensitive material, drying the coat, firing the coat at a temperature of 750° C. to 870° C. to form the humidity-sensing part of the humidity-sensing element, and treating the surface of said humidity-sensing part with KOH or $Na_2CO_3$.

8. A process for fabricating a humidity-sensing element which comprises forming an electrode layer on at least one side of a ceramic substrate, applying to the electrode layer a coat of a humidity-sensitive paste containing a ceramic comprising $ZrO_2$, $Y_3O_3$, or mixtures thereof as a humidity-sensitive material, drying the coat, firing the coat at a temperature of 750° C. to 870° C. to form the humidity-sensing part of the humidity-sensing element, and housing said humidity-sensing element in a case equipped with a filter film of a chlorinated polymer.

9. A process according to claim 8 wherein said filter film has a porosity of 35 to 85%, a pore size of 0.01 to 3 $\mu$m, and a thickness of 20 to 200 $\mu$m.

10. A humidity-sensing element fabricated by a process according to any one of claims 1-9.

11. A process according to claims 3, 5, 7 or 8 wherein said electrode layer is formed by screen printing or vapor deposition of gold.

* * * * *